(12) United States Patent
Anctil

(10) Patent No.: US 6,539,632 B2
(45) Date of Patent: Apr. 1, 2003

(54) LONG HANDLE TOENAIL CLIPPER

(75) Inventor: Rene Anctil, North Kingstown, RI (US)

(73) Assignee: Holistic Center of Antioch, Inc., North Kingstown, RI (US)

( * ) Notice: Subject to any disclaimer, the term of this patent is extended or adjusted under 35 U.S.C. 154(b) by 0 days.

(21) Appl. No.: 09/760,542

(22) Filed: Jan. 16, 2001

(65) Prior Publication Data

US 2002/0092170 A1 Jul. 18, 2002

(51) Int. Cl.⁷ ............................................. A45D 29/00
(52) U.S. Cl. ................... 30/28; 30/131; 30/251
(58) Field of Search ............................ 30/28, 131, 251, 30/250; 132/73, 73.5, 75.3, 75.4, 75.5

(56) References Cited

U.S. PATENT DOCUMENTS

| | | | | |
|---|---|---|---|---|
| 111,738 A | * | 2/1871 | Gaines et al. | 30/251 |
| 245,122 A | * | 8/1881 | Bishop | 30/251 |
| 756,227 A | * | 4/1904 | Pisk | 30/251 |
| 804,426 A | * | 11/1905 | Mullen | 30/251 |
| 857,790 A | * | 6/1907 | Carroll | 132/73.6 |
| 1,135,989 A | * | 4/1915 | Breach | 30/251 |
| 1,175,683 A | * | 3/1916 | Beach et al. | 30/250 |
| 1,372,670 A | * | 3/1921 | Corrow | 30/251 |
| 1,647,085 A | * | 10/1927 | Dearborn | 30/251 |
| 1,784,022 A | * | 12/1930 | Minikhiem | 30/251 |
| 1,823,199 A | * | 9/1931 | Huxman | 30/251 |
| 2,547,433 A | * | 4/1951 | Barnett | 30/250 |
| 2,564,148 A | * | 8/1951 | Broderick | 30/251 |
| 3,203,094 A | * | 8/1965 | Couture | 30/250 |
| 3,389,462 A | * | 6/1968 | Bowers | 30/138 |
| 3,718,333 A | * | 2/1973 | Santoro et al. | 473/229 |
| 3,768,363 A | * | 10/1973 | Tackett et al. | 30/293 |
| 4,182,390 A | * | 1/1980 | Renner | 30/312 |
| D286,091 S | * | 10/1986 | Hill | D24/147 |
| 4,847,994 A | * | 7/1989 | Dunn, Jr. | 132/73 |
| 4,893,406 A | * | 1/1990 | Larson | 30/177 |
| 5,342,055 A | * | 8/1994 | Diley | 473/208 |
| 5,357,677 A | * | 10/1994 | West | 132/73.5 |
| 5,775,340 A | * | 7/1998 | Rains | 132/73.5 |
| 5,832,610 A | * | 11/1998 | Chaplick | 132/75.2 |
| 5,997,408 A | * | 12/1999 | Bankhead | 473/227 |
| 6,183,372 B1 | * | 2/2001 | Anderegg, Jr. | 473/131 |
| 6,220,251 B1 | * | 4/2001 | Jeong et al. | 132/73.5 |

* cited by examiner

*Primary Examiner*—Allan N. Shoap
*Assistant Examiner*—Jason Prone
(74) *Attorney, Agent, or Firm*—Salter & Michaelson

(57) ABSTRACT

A balanced Long Handle Toenail Clipper for allowing a person to cut their toenails without the need to bend over or stand, including a cylindrical tubular housing which encloses a plunger rod, finger grips which are attached to the tubular housing, and a nail clipper having a cutting portion and an actuating lever. A stabilizing arm coupled to the tubular housing adds balance to the device and provides an individual with a clear view of the toenail clipper. A magnifying glass coupled to the tubular housing facilitates viewing of the clipping operation, and a plunger rod is adapted to engage the actuating lever of the nail clipper to effect operation of the latter.

7 Claims, 2 Drawing Sheets

LONG HANDLE TOENAIL CLIPPER

BACKGROUND OF THE INVENTION

1. Field of the Invention

The present invention relates to toe nail clippers and more particularly to a new and improved long handled toenail clipper for allowing a person to cut their toenails without need to bend over or stand. Many elderly, overweight, and physically disabled individuals have extreme difficulty in trimming their toe nails with conventional forms of toenail clippers.

2. Description of the Prior Art

The use of toe nail clippers is known in the prior art. Toe nail clippers heretofore devised and utilized are known to consist basically of familiar, expected and obvious structural configurations, notwithstanding the myriad of designs encompassed by the crowded prior art which have been developed for the fulfillment of countless objectives and requirements. Known prior art toe nail clippers include U.S. Pat. No. 4,847,994 to DunnJr.; U.S. Pat. No. 4,893,406 to Larson; U.S. Pat. No. 5,357,677 to West; U.S. Pat. No. 5,546,658 to Macleod; U.S. Pat. No. 5,775,340 to Rains.

While these devices fulfill their respective, particular requirements, the limitations of the prior art is that it requires the user to bend over or stand to operate the devices. As the prior art in long handle toenail clippers was intended for use by the elderly, overweight, and physically challenged, lack of balance, the necessity of and standing to use the prior art becomes challenging to the user. Instead of an assisting aid, the aforementioned patents do not disclose a new long handle toenail clipper. The device of the instant invention includes a conventional sided nail clipper having a cutting portion and an actuating lever; a plunger rod coupled to the actuating lever of the nail clipper; a stabilizing arm coupled to a tubular housing; and a magnifying glass coupled to the tubular housing.

In these respects, the long handle toenail clipper according to the present invention substantially departs from the conventional concepts and designs of the prior art, and in so doing provides an apparatus primarily developed for the purpose of allowing a person to cut their toenails without needing to bend over or stand.

SUMMARY OF THE INVENTION

In view of the foregoing disadvantages inherent in the known types of Long Handle Toe Nail Clippers now present in the prior art, the present invention provides a new Long Handle Toe Nail Clipper which has all the advantages of the prior art toe nail clippers and none of the disadvantages by allowing a person to cut their toenails without needing to bend over or stand.

The general purpose of the present invention, which will be described subsequently in greater detail, is to provide a new long handle toenail clipper apparatus and method which has many of the advantages of the toe nail clippers mentioned heretofore and many novel features that result in a new long handle toenail clipper which is not anticipated, rendered obvious, suggested, or even implied by any of the prior art toe nail clippers, either alone or in any combination thereof.

To attain this, the present invention generally comprises a conventional nail clipper having a cutting portion and an actuating lever; a cylindrical tubular housing which encloses a plunger rod; a stabilizing arm pivotally coupled to the housing; and a locking knob extending through the top portion of the stabilizing arm connector and the housing for selectively locking the stabilizing arm to allow pivotal rotation. A magnifying lens is coupled with respect to the lower portion of the tubular housing disposed above the nail clipper. The magnifying lens has an open end clasp portion slidably receiving the lower portion of the tubular housing. A locking knob extends through the outer end and lower portion of the clasp for selectively locking the magnifying lens with respect to the lower portion to preclude sliding of the lens.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawing. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of this invention. It is important, therefore, that the claims be regarded as including such equivalent constructions insofar as they do not depart from the spirit and scope of the present invention.

Further, the purpose of the foregoing Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract is neither intended to define the invention of the application, which is measured by the claims, nor is it intended to be limiting as to the scope of the invention in any way.

It is therefore an object of the present invention to provide a new long handle toenail clipper apparatus and method which has many of the advantages of the toe nail clippers mentioned heretofore and many novel features that result in a new long handle toenail clipper which is not anticipated, rendered obvious, suggested, or even implied by any of the prior art toenail clippers, either alone or in any combination thereof.

It is another object of the present invention to provide a new long handle toenail clipper which may be easily and efficiently manufactured and marketed.

An even further object of the present invention to provide a new long handle toenail clipper which is of durable and reliable construction.

An even further object of the present invention is to provide a new long handle toenail clipper which is susceptible of a low cost of manufacture with regard to both materials and labor, and which accordingly is then susceptible of low prices of sale to the consuming public, thereby making such long handle clippers economically available to the buying public.

Still yet another object of the present invention is to provide a new long handle toenail clipper which provides in the apparatuses and methods of the prior art some of the advantages thereof, while simultaneously overcoming some of the disadvantages normally associated therewith.

Still another object of the present invention is to provide a new long handle toenail clipper for allowing a person to cut their toe nails without needing to bend over or stand.

Yet another object of the present invention is to provide a new long handle toenail clipper which includes a sided conventional nail clipper having a cutting portion and an actuating lever. A stabilizing arm is positioned above and is secured to a tubular housing. The stabilizing arm addresses the user's necessity for balance. A plunger rod is coupled to the actuating lever of the nail clipper for operating the clipper.

Still yet another object of the present invention is to provide a new long handle toenail clipper that can be designed with a magnifying glass to aid persons whose vision is impaired.

Even still another object of the present invention is to provide a new long handle toenail clipper that will aid the overweight, the elderly and th e physically challenged.

These together with other objects of the invention, along with the various features of novelty which characterize the invention, are pointed out with particularity in the claims annexed to and forming a part of this disclosure. For a better understanding of the invention, its operation advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
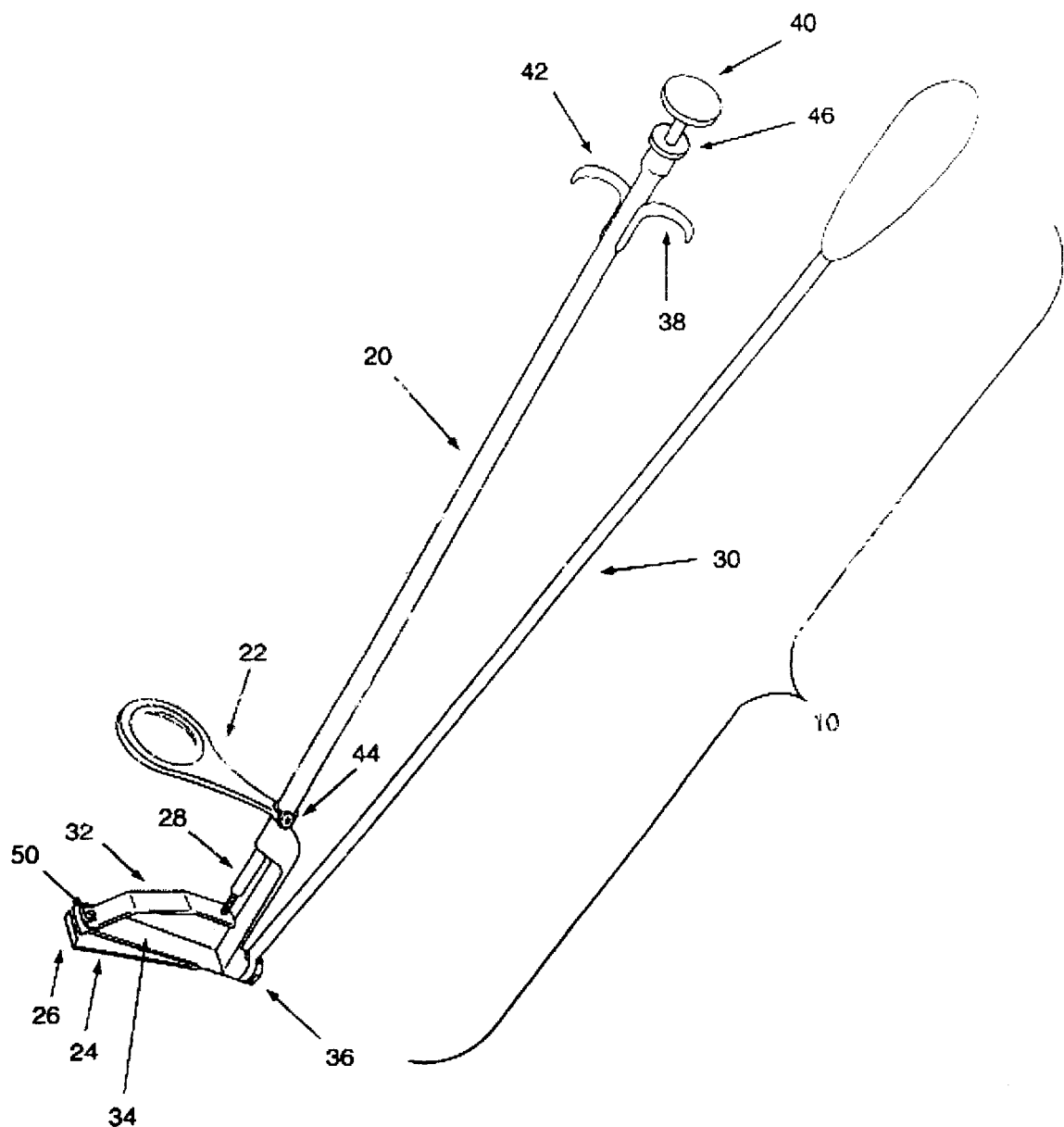
FIG. 1 is a perspective view of the nail clipper apparatus of the present invention.

FIG. 1 illustrates a long handle toe nail clipper according to the present invention. Nail clipper apparatus 10 includes an elongated tubular body 20 having plunger rod 28 extending therethrough. Attached to the top end of elongated body 20 are finger grips 38 and 42. Attached to the top of plunger rod 28 is palm grip 40. The bottom of plunger rod 28 engages actuating lever 32. At the top of elongated body 20 is guide 46 which keeps plunger rod 28 centered in elongated body 20. At the bottom of elongated body 20 is a leaf spring type toenail clipper having a pair of parallel spaced spring steel cutting portions 26 and 34 which are connected by pin 50 which allows the cutting portions 26 and 34 to be moved together and apart. An actuating lever 32 is connected in conventional fashion to the pin 50 for the purpose of trimming the toenail. A sided flange 24 on each side of the clipper retains nail clippings. When plunger rod 28 is pushed downwardly, the clipper cutting jaws 26 and 34 are forced together cutting a nail placed between the jaws, in a manner well known in the art.

Pivotally mounted adjacent the rear end of the clipper is a stabilizing arm 30 connected and secured with lock knob 36. A magnifying glass 22 may be slidably mounted on elongated body 20 to provide a magnified image of the toe and clipper.

Figure 2:
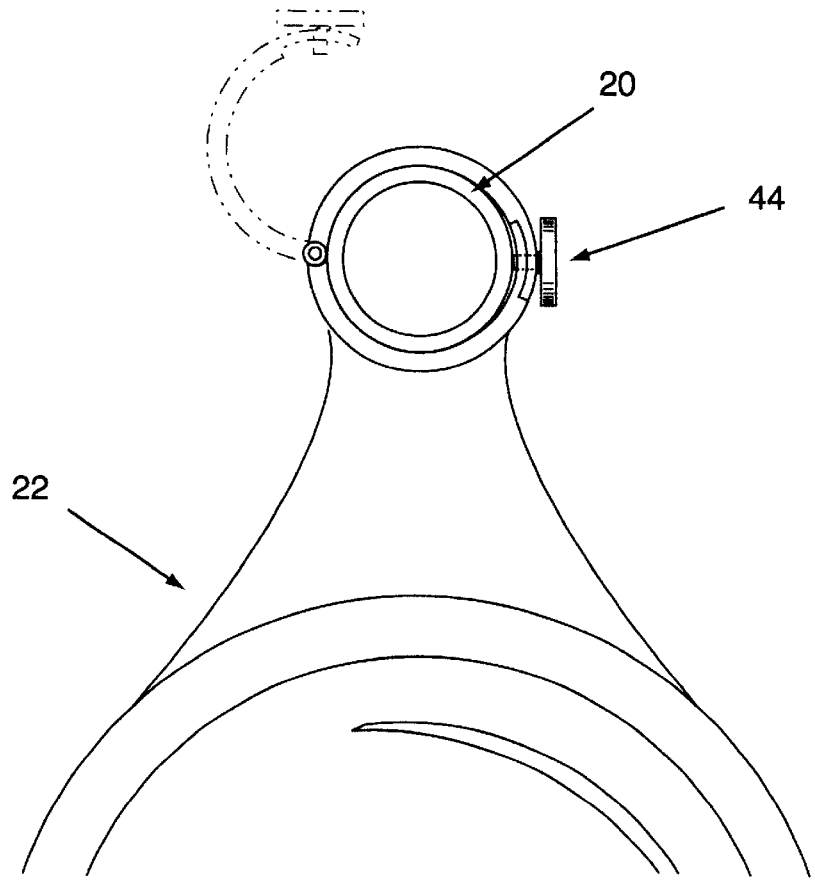
FIG. 2 is an enlarged fragmentary view illustrating the wrap-around feature (clasp) of the magnifying lens.

FIG. 2 is a top plan view of the nail clipper illustrating the wrap-around feature of magnifying glass 22 secured with lock knob 44 to elongated body 20.

Figure 3:
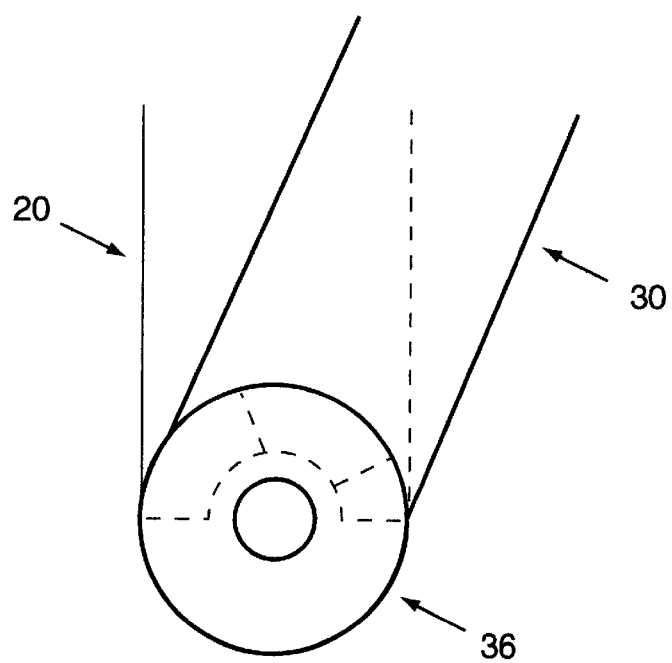
FIG. 3 is a schematic top view of the nail clipper apparatus showing the pivotal aspect of the stabilizing arm.

FIG. 3 is a schematic top view of the nail clipper apparatus showing the pivotal aspect of stabilizing arm 30 attached to elongated body 20 with lock knob 36.

As to a further discussion of the manner of usage and operation of the present invention, the same should be apparent from the above description. Accordingly no ether discussion relating to the manner of usage and operation will be provided. With respect to the above description then it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification, are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A long handle toenail clipper for permitting a person to cut their toenails without having to bend all the way over, comprising:

a nail clipper having normally spaced cutting edges, and an actuating lever for moving said cutting edges toward each other to effect the desired cutting action;

an elongated cylindrical tubular housing mounted above said clipper having a plunger rod slidably mounted therein for movement toward said lever to actuate same;

a stabilizing arm pivotally connected at a point adjacent the opposite end of said clipper from said cutting edges, said stabilizing arm extending upwardly in substantially parallel relation to said tubular housing and selectively swingable sidewise with respect thereto to a desired position wherein gripping of the stabilizing bar with one hand holds the clipper steady without obstructing the user's view of the clipper, while the other hand operates the plunger rod; and means for retaining said stabilizing bar in its selected operative position.

2. The clipper of claim 1 wherein said retaining means comprises a locking knob.

3. The clipper of claim 1 further comprising cooperating handle means adjacent to but below the top end of said tubular housing and further handle means at the top end of said plunger rod, whereby said further handle means may be actuated using only one hand.

4. The clipper of claim 1 further comprising a magnifying lens mounted on said tubular housing above and in alignment with said clipper.

5. The clipper of claim 4 wherein said lens is slidably movable with respect to said tubular housing to permit adjustment of its height with respect to said clipper, and means for retaining said lens in its selected position.

6. The clipper of claim 5 wherein said retaining means comprises a locking knob.

7. The clipper of claim 3 wherein the handle means at the top end of the plunger rod is a palm grip, and the handle means adjacent to but below the top end of the tubular housing is a finger grip.

* * * * *